(12) United States Patent
Graichen

(10) Patent No.: US 9,995,310 B2
(45) Date of Patent: Jun. 12, 2018

(54) ROTARY PUMP COMPRISING A ROTOR AND DELIVERY ELEMENTS

(75) Inventor: Kurt Graichen, Berlin (DE)

(73) Assignee: BERLIN HEART GMBH, Berlin (DE)

( * ) Notice: Subject to any disclaimer, the term of this patent is extended or adjusted under 35 U.S.C. 154(b) by 613 days.

(21) Appl. No.: 14/237,359

(22) PCT Filed: Aug. 8, 2012

(86) PCT No.: PCT/EP2012/065541
§ 371 (c)(1),
(2), (4) Date: Mar. 28, 2014

(87) PCT Pub. No.: WO2013/021014
PCT Pub. Date: Feb. 14, 2013

(65) Prior Publication Data
US 2014/0205434 A1    Jul. 24, 2014

Related U.S. Application Data

(60) Provisional application No. 61/521,811, filed on Aug. 10, 2011.

(30) Foreign Application Priority Data

Aug. 10, 2011  (EP) .................................... 11075191

(51) Int. Cl.
*F04D 29/18*   (2006.01)
*F04D 3/02*    (2006.01)
(Continued)

(52) U.S. Cl.
CPC ......... *F04D 29/183* (2013.01); *A61M 1/1015* (2014.02); *A61M 1/1017* (2014.02);
(Continued)

(58) Field of Classification Search
CPC ...... F04D 3/02; F04D 13/0646; F04D 29/183; F04D 29/186; A61M 1/101; A61M 1/1015; A61M 1/1017
See application file for complete search history.

(56) References Cited

U.S. PATENT DOCUMENTS 1,586,978 A    6/1926   Dorer
5,055,005 A   10/1991   Kletschka
(Continued)

FOREIGN PATENT DOCUMENTS

CN    1364213 A     8/2002
CN    101520050 A   9/2009
(Continued)

*Primary Examiner* — Audrey K Bradley
(74) *Attorney, Agent, or Firm* — Brinks Gilson & Lione

(57) ABSTRACT

A rotary pump includes a rotor having delivery elements which deliver at least a portion of a fluid in an axial direction of the rotor. Two delivery elements or groups of delivery elements are provided on the rotor for delivering the fluid, and deliver the fluid to be delivered in mutually opposing axial directions of the rotor, so that the axial thrust components substantially compensate each other. The fluid flows flowing counter to each other jointly give way in the radial direction of the rotor and can be jointly discharged through the volute casing and utilized.

15 Claims, 4 Drawing Sheets

(51) Int. Cl.
 *F04D 13/06* (2006.01)
 *A61M 1/10* (2006.01)
 *A61M 1/12* (2006.01)

(52) U.S. Cl.
 CPC .......... *F04D 3/02* (2013.01); *F04D 13/0646* (2013.01); *F04D 29/186* (2013.01); *A61M 1/101* (2013.01); *A61M 1/1031* (2014.02); *A61M 1/122* (2014.02)

(56) References Cited

U.S. PATENT DOCUMENTS

| | | | |
|---|---|---|---|
| 5,158,440 A | 10/1992 | Cooper et al. | |
| 5,470,208 A | 11/1995 | Kletschka | |
| 5,938,412 A * | 8/1999 | Izraelev | A61M 1/1015 415/206 |
| 6,866,625 B1 * | 3/2005 | Ayre | A61M 1/101 415/182.1 |
| 2004/0234391 A1 | 11/2004 | Izraelev | |
| 2006/0122456 A1 | 6/2006 | LaRose et al. | |

FOREIGN PATENT DOCUMENTS

| | | | |
|---|---|---|---|
| CN | 101730552 A | 6/2010 | |
| DE | 1653802 | 8/1971 | |
| DE | 3217341 A1 * | 3/1983 | .............. F16C 17/02 |
| EP | 0081872 A2 | 6/1983 | |
| EP | 0081872 A3 | 11/1983 | |
| FR | 2220696 | 10/1974 | |
| GB | 1147288 | 4/1969 | |
| GB | 1458693 | 12/1976 | |
| WO | WO 94/13955 | 6/1994 | |
| WO | WO 2006/131425 A1 | 12/2006 | |

\* cited by examiner

ROTARY PUMP COMPRISING A ROTOR AND DELIVERY ELEMENTS

CROSS-REFERENCE TO RELATED APPLICATIONS

This application is a 371 nationalization of PCT/EP2012/065541, which in turn claims benefit of European patent application 11075191.4 filed on Aug. 10, 2011 and U.S. provisional application 61/521,811 filed on Aug. 10, 2011.

BACKGROUND

The invention is in the field of mechanics, and more particularly pump technology, and relates to rotary pumps.

Such rotary pumps are known in the form of axial flow pumps and radial flow pumps, in each case comprising rotors which contain delivery elements, for example in the form of blades. Depending on the geometric shapes of the delivery elements/blades, delivery of a fluid takes place primarily in the axial direction, in the radial direction or in mixed directions.

Such rotary pumps can advantageously be used, for example, in medical technology for delivering endogenous liquids, for example as blood pumps.

Notably in the case of axial flow pumps, the question in regard to the quality and type of bearing arrangement arises. Because such pumps often run very fast, for example at up to 10,000 or 20,000 rpm, and only minimal abrasion should be incurred, and because additionally the heat development, wear and tear, as well as the energy consumption of such a pump are to be minimized, the bearing arrangement is subject to increased requirements.

It is especially difficult to find a simple and cost-effective solution for the axial bearing arrangement.

It is therefore the object of the invention to create a rotary pump of the type mentioned above, which poses the lowest possible requirements in regard to the bearing arrangement while having a simple design.

SUMMARY

For this purpose, delivery elements are provided on the rotor of the rotary pump, which deliver the fluid to be delivered in the axial direction of the rotor in a first sense of direction, and additional delivery elements are provided on the rotor, which deliver the fluid likewise in the axial direction, but in the opposite sense of direction. The respective delivery elements are preferably disposed on the circumference of the rotor.

The respective generated axial thrust forces of the two delivery elements, or groups of delivery elements, acting in opposite directions thus act likewise in opposite directions and, ideally, cancel each other out. This results in minimized axial thrust of the pump, despite axial delivery of a fluid.

The rotor is hollow and comprises a hub having a cavity, within which a fluid channel is formed, which in a first axial region, and more particularly at a first end-face end of the hub, has an intake opening and in a second axial region, and more particularly at a second end-face end, has a discharge opening. The fluid channel is designed to be continuous in the axial direction, and the openings can advantageously be implemented at the end faces, but also radially on the outer surface-side in the axial end regions.

The fluid channel can be designed as a centric borehole in the hub, preferably having a circular cross-section, which is preferably constant over the length. However, it is also possible for the hub to have a cylindrical cavity, the outer surface of which is rotatably mounted on an inner hollow cylinder, which is designed slightly smaller in terms of the diameter. The inner hollow cylinder can then be connected to the pump housing in a stationary manner and the cavity thereof can form the continuous fluid channel.

According to the remaining variants of the pump, the rotor itself forms the fluid channel in the hub and the rotor is magnetically and/or hydrodynamically mounted on the pump housing.

The rotor diameter and/or the active, delivering cross-sectional surfaces of the delivery elements, as seen looking in the flow direction, should advantageously be the same for the one and the other delivery elements, in particular differ by less than 50% of the respective larger surface, and preferably by no more than 10%.

It is additionally advantageous if the two fluid flows differ by no more than 50% of the larger fluid flow, preferably by less than 30%, more preferably by less than 20%, and more particularly by less than 10%.

In the region of the one and the other delivery elements, the hub can have substantially the same diameter, wherein the differences should be less than 20% of the larger diameter, and more particularly less than 5% of the larger diameter.

In general, it must of course also be assured that the fluid flows having opposite directions are controlled such that a resulting collective flow of the fluid is created, which corresponds to the desired delivery. However, this control or guidance of the fluid flows can take place without generating additional axial forces acting on the rotor, as will be described hereafter based on exemplary embodiments of the invention.

In particular, it may be advantageous for the first fluid flow delivered by the first delivery element, or a first group of delivery elements, and the second fluid flow delivered by the second delivery element, or a second group of delivery elements, to be separated from each other.

To this end, it may be advantageous for the first and second fluid flows to be separated from each other before the contact with the first and further delivery elements, or the first and second groups of delivery elements.

This can be achieved, for example, by the first delivery element, or the first group of delivery elements, and the further delivery element or elements taking in the fluid from different regions of a fluid reservoir and delivering the same separately from each other. The fluid flows thus separated can then be suitably merged after delivery by the respective delivery elements.

According to an advantageous implementation of the invention, the first and second fluid flows are combined after passing through the first and further delivery elements, or a first and a second group of delivery elements.

For this purpose, the first and second delivery elements, or the first and second groups of delivery elements, may deliver the first and second fluid flows in a way directed toward each other, and the first and second fluid flows may be deflected jointly radially to the outside.

For example, the first delivery element, or a first group of delivery elements, can be formed by delivery blades or by an individual delivery blade disposed helically about a rotor hub, the blades alone or in cooperation effecting an axial delivery of the fluid. The further delivery element or elements can also be designed like the first delivery element or elements, however in an accordingly reversed arrangement, so that delivery takes place in an axially opposite direction. Ideally, the respective generated axial thrust of the different groups of delivery elements should be the same in terms of the magnitude. This can be achieved by designing the delivery elements to be inversely the same or, for example, by providing the first delivery elements with a different pitch, however with a correspondingly different, adapted surface or distribution over the axial length of the rotor, than the second group of delivery elements. The manner for creating the corresponding axial thrust can thus be different because of the different geometric shapes of the delivery elements, wherein by nature the rotational speed of all delivery elements is the same because of the arrangement on a common rotor, and wherein additionally the generated axial thrust should be the same in terms of magnitude, to the extent possible.

If the fluid flows, which have opposing directions and flow toward each other and which are generated by the different groups of delivery elements, are guided toward each other on the circumference of the rotor, this automatically results in a radial deflection, for example to the outside or in the circumferential direction. An interface is formed between the partial flows when they mix, along which interface the partial flows run parallel to each other and optionally likewise mix.

In addition, a guide device can advantageously be attached to the rotor for deflecting the fluid flows from the axial direction in the radial direction. This device can be formed by an annual peripheral elevation on the rotor, having concave oblique stop faces on both sides. However, it is also possible to simply provide a circular ring on the rotor, the ring having a triangular design in the radial section.

For discharging the fluid flow, the first and further delivery elements are advantageously disposed in different sections of the rotor and a volute casing (outlet housing) is provided axially between these sections, which surrounds the rotor. Such a volute casing can be easily formed by a peripheral expansion of the pump housing with an integrated radial outlet. The peripheral outer surface of this expansion can also have the geometric shape of a spiral so as to support the discharging of the fluid.

According to a particularly advantageous embodiment of the invention, several separate fluid channels are provided within the pump housing, which connect a fluid chamber to various axial sections, and more particularly the ends, of the rotor. Each of the various axial sections of the rotor on which delivery elements delivering in opposite directions are disposed can thus be supplied with separately inflowing fluid flows.

It is also possible for the rotor, together with the various groups of delivery elements, to deliver two respective fluid flows axially to the various ends of the rotor and to take in the fluid in the overall in the radial direction in the axially central region of the rotor. In this case, the separate fluid flows can flow out via the various fluid channels and be combined in a fluid chamber.

It is particularly advantageous for the hub of the rotor to be hollow and form a fluid channel. In this case, the rotor can take in the fluid at one of the end-face ends, wherein a first portion of the fluid flow flows along in the radially outer region of the rotor and a second portion flows through the interior of the rotor hub to the opposite end of the rotor. There, at the opposite end of the rotor, this fluid flow, after a deflection, impinges on the further delivery elements which cause an opposite delivery in the axial direction and deliver the fluid flow delivered there in the opposite direction counter to the first fluid flow.

By suitably shaping the deflection element, the deflection can also suitably influence the inflow to the delivery elements by generating a prerotation.

To this end, stationary guide device for fluid flows may be provided on stationary parts of the rotor pump. For example, it may be provided in detail that a baffle is disposed in the axial extension of the rotor hub, provided the hub is hollow, as a guide device for deflecting a fluid flow from an axial direction into one or more radial directions, notably comprising a central elevation. The central elevation can, for example, be a cone or have a cone-like shape, advantageously comprising concave flanks.

In particular stationary guide vanes can be provided on one side or both sides in the extension of the rotor as further guide devices for the fluid flows, which can be either straight guide vanes or helically disposed guide vanes, whereby the overall helically oriented fluid flow can be optimized along the rotor. A suitable prerotation during the inflow onto the delivery elements can thus be created.

In any case, the aforedescribed generation and orientation or guidance of fluid flows allows the resulting total axial thrust acting on the rotor to be decreased, so that less complex thrust bearing designs than in the existing customary solutions can be selected. For example, it is possible to use active or passive axial magnetic bearings or controlled magnetic bearings. In general, the magnetic elements of an electric motor drive of a rotor can also be used for implementing an axial magnetic bearing. These elements alone can advantageously already suffice.

BRIEF DESCRIPTION OF THE DRAWINGS

The invention will be shown and then described hereafter based on an exemplary embodiment in drawings. In the drawings.

DESCRIPTION OF PREFERRED EMBODIMENTS

Figure 1:
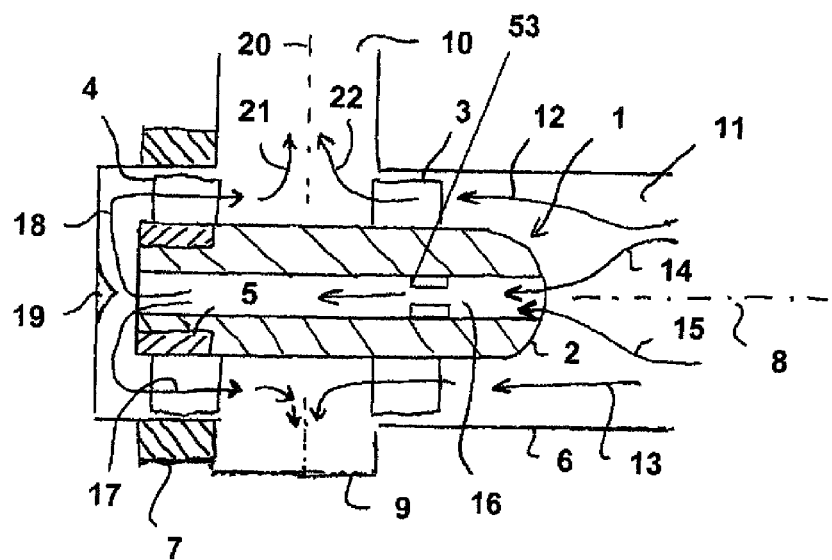
FIG. 1 shows a schematic view of a longitudinal section of a rotary pump comprising a hollow rotor.

FIG. 1 is a schematic view of a longitudinal section of a rotary pump, comprising a rotor 1, which has a hub 2 as well as first delivery elements 3 and second or further delivery elements 4 on the circumference. A bearing arrangement of the rotor is not shown in detail, however schematically an axial magnetic bearing arrangement is indicated by a magnet 5, which is introduced in the hub 2 and rotates accordingly, and a stationary stator magnet 7, which is attached to the outside on the pump housing 6. No additional bearing elements are shown, however examples of mountings will be described in more detail below.

The magnet 5 can also be designed as a rotor magnet of an electric motor drive, wherein then a stator winding must be provided on the housing.

The pump housing 6 has a substantially cylindrical design, with rotational symmetry about the axis 8.

In the region of the rotor 1, the housing 6 is surrounded by a so-called volute casing 9, into which the fluid to be delivered is delivered radially toward the outside starting from the rotor 1. The volute casing 9 has a radial outlet 10 on the circumference in a limited region. In the example shown, a fluid, for example blood, is present in the fluid chamber 11 of the pump housing 6 and is suctioned from there into the region of the delivery elements 3, 4. First arrows 12, 13 indicate that the fluid is suctioned to the first delivery elements 3, which can be implemented, for example, as delivery blades distributed on the circumference of the rotor hub 2. The delivery blades 3 effect a substantially axial delivery along the rotor hub 2 in the direction of the arrows 12, 13.

In addition, the hub 2 has a cavity 16, which is formed in the interior of the hub in a concentrically continuous manner and into which the fluid is suctioned, as is indicated by the second arrows 14, 15. As a result, the further delivery elements 4 cause the fluid to be delivered in the axial direction, which is to say parallel to the longitudinal axis 8 of the rotor, but in the opposite direction of the delivery of the first delivery elements 3, as is indicated by the arrows 17, 18. The fluid is thus taken in at the end of the rotor 2, and the suction continues to the fluid chamber 11. The suctioned fluid is deflected at the end of the rotor 1 facing away from the fluid chamber 11 by a guide or deflection element 19, which can be designed as a kind of baffle having a conical structure, for example also having concave flanks. From there, the fluid flow is deflected from the axial direction 14, 15 in a radial direction and then by a total of approximately 180° to the delivery elements 4.

The cavity/fluid channel 16 can be continuous, having smooth walls, as a cylindrical cavity, however so as to support the delivery of fluid, it may also comprise delivery elements, for example in the form of delivery blades 53, on the inside wall. Because these, due to the generated thrust, can create an axial force on the rotor, it is useful to take the developing forces into consideration in the dimensioning of the remaining delivery elements 3, 4 so as to balance the sum of axial forces to as great an extent as possible.

In the region of the interface indicated by the dotted line 20, the two axial fluid flows from the delivery elements 3, 4 axially impinge on each other and are deflected in the radial direction, as is indicated by the arrows 21, 22. Here, in addition to the radial component, the fluid flow has an azimuthal component, so that the volute casing 9 can also utilize the azimuthal component to deliver a fluid flow through the outlet 10 radially out of the pump.

Despite axial intake and two groups of delivery elements 3, 4 axially delivering in opposite directions, a delivery flow of a fluid can thus be created, wherein the axial thrust forces acting on the delivery elements cancel each other at least partially, and ideally completely. The axial bearing arrangement, which is schematically indicated by the magnets 5, 7, can thus be minimized in terms of the design complexity thereof.

Figure 2:
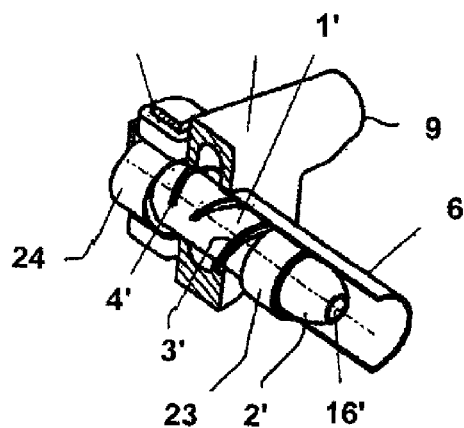
FIG. 2 is a three-dimensional view of a rotary pump comprising an open housing.

FIG. 2 is a schematic view of a three-dimensional embodiment of a similar rotary pump as in FIG. 1 with a few design differences. A part of the volute casing 9 is shown in an open view and a rotor 1' comprising delivery elements 3', 4' having inverted designs are visible.

The rotor 1' has a longitudinally continuous cavity 16' in the hub 2'. In addition, the rotor 1' comprises what are known as support rings 23, 24, which rotate accordingly on the rotor and can be mounted on the wall of the pump housing 6, for example hydrodynamically. The suctioned fluid, which in the example above is blood, can flow freely as a main delivery flow in the main flow channel between the support rings 23, 24 and the rotor hub 2', while a secondary flow between the support rings and the wall of the pump housing flows through, forming a stabilized liquid layer acting as a sliding layer, whereby a hydrodynamic bearing is formed.

Figure 3:
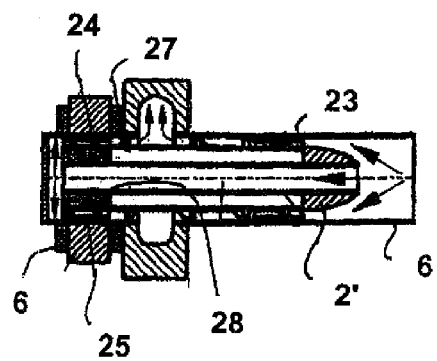
FIG. 3 is a longitudinal section of a rotary pump comprising a hollow rotor and a bearing device.

FIG. 3 shows the pump illustrated in a three-dimensional image in FIG. 2 again in a longitudinal section. The support rings 23, 24 are apparent there in the region between the rotor hub 2' and the housing 6. In addition, a more complex magnetic bearing arrangement comprising a control coil 25, two stator magnets 26, 27 and a rotor magnet 28 is shown. This controlled magnetic bearing arrangement is used to axially position and mount the rotor hub 2'.

Figure 4:
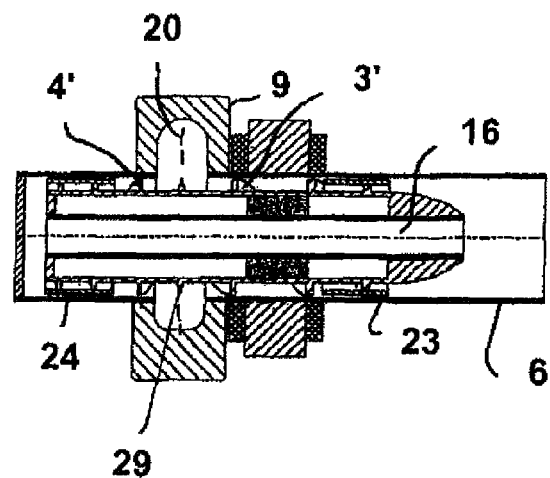
FIG. 4 is a longitudinal section of a rotary pump comprising a rotor, which has support rings for mounting, and a magnetic bearing.

FIG. 4 shows a longitudinal section of a rotary pump comprising a hollow rotor, which in the interior has a channel 16 for a portion of the fluid, and first delivery elements 3' and second delivery elements 4', which deliver the fluid in mutually oppositely directed axial directions on the circumference of the rotor. In the region of the ends, the rotor has two support rings 23, 24, which effect radial mounting on the housing 6.

Inside the volute casing 9, a guide device 29 having the shape of a circular fin extending around the circumference of the rotor is shown in the region of the interface 20, where the two partial fluid flows delivered by the delivery elements 3', 4' merge, the fin deflecting the respective fluid flows, which flow in axially from both sides, at least partially in radial directions.

Figure 5:
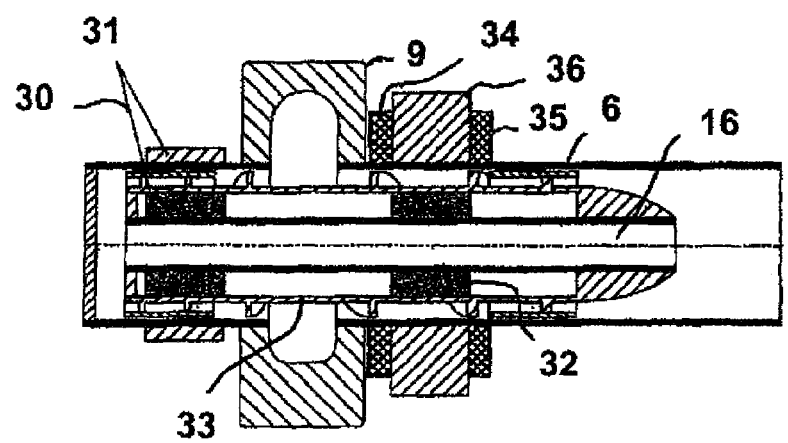
FIG. 5 is a longitudinal section of a rotary pump similar to that of FIG. 4, comprising a plurality of magnetic bearing devices.

The rotary pump shown schematically in FIG. 5 dispenses with a guide device 29, whereby the two partial flows axially impinging on each other in the region of the volute casing 9 are jointly deflected radially along a flow boundary. FIG. 5 specifically shows a more complex magnetic bearing arrangement comprising a passive magnetic bearing, which has a magnetic ring 30 in the rotor and an iron ring 31 on the outside on the pump housing 6.

In addition, the rotor has a magnetic ring 32, which likewise is attached to the rotor and is disposed in the interior thereof in a ring-shaped manner between the cylindrical cavity 16 and a cylindrical outer panel 33 carrying the delivery elements and which cooperates with an active magnetic bearing device having two ring magnets 34, 35 and a control coil 36, by means of which the magnetic field strength can be controlled.

Moreover, a sensor for picking up the axial position of the rotor may be provided, which measures the current axial position of the rotor and feeds it to a control process as a controlled variable.

Figure 6:
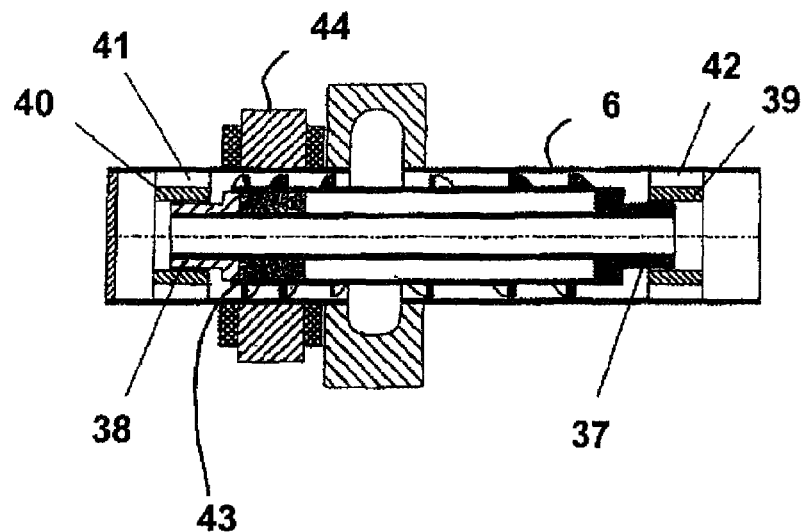
FIG. 6 is a longitudinal section of a rotary pump comprising a hollow rotor, a bearing device and stationary guide vanes.

FIG. 6 shows another variant of a rotary pump, in which the ends 37, 38 of a rotor are mounted in radial bearing points 39, 40, which additionally on the outside carry stationary guide vanes 41, 42 between the bearing and the housing wall of the housing 6. The guide vanes are positioned and shaped such that they create a suitable pre-orientation of the fluid flow (prerotation) before the partial fluid flows flow into the region of the delivery elements. The rotor additionally comprises a magnetic body 43, which cooperates with an actively controlled magnetic bearing 44 to form an axial bearing arrangement.

Figure 7:
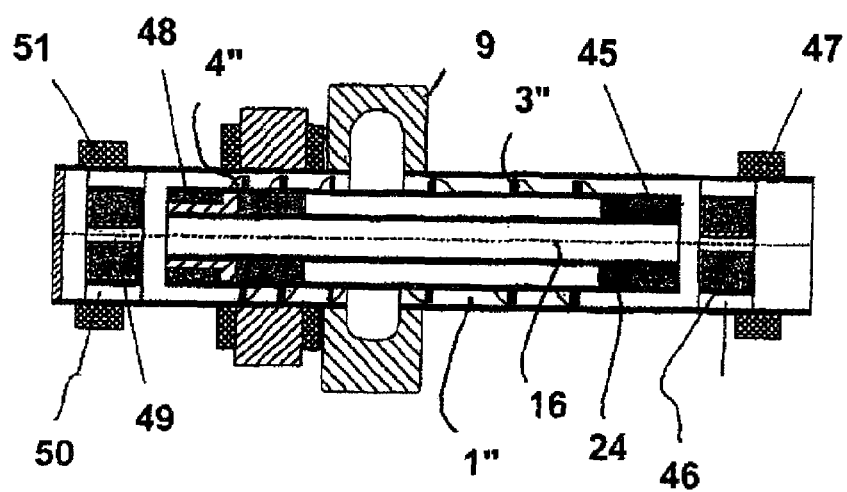
FIG. 7 shows a further longitudinal section of a rotary pump comprising a hollow rotor and an active magnetic bearing device disposed axially thereto.

FIG. 7 shows a rotary pump comprising a rotor 1″, which has two groups of delivery elements 3″, 4″ acting in opposite directions, wherein a partial fluid flow flows through a cavity 16 of the hollow hub 2″ before the flow is deflected and guided to the delivery elements 4″.

The rotor is provided at both ends with two active magnetic bearing arrangements. At the first end, the rotor has a magnetic ring 45, which interacts with a stationary magnetic ring 46. In addition, the stationary magnetic ring 46 is controlled by a control coil 47.

At the opposite end of the rotor, a magnetic ring 48 is also provided in the rotor, the ring cooperating with a stationary magnetic ring 49 in the housing, wherein the magnetic ring 49 has guide vanes on the outside on the circumference and cooperates with a control coil 51 disposed on the outside on the housing of the pump so as to form a controlled axial bearing.

The arrangement thus has two controlled axial bearings at the ends of the rotor and axial thrust compensation on the rotor as a result of two groups of delivery elements which deliver in opposite directions.

The performance and the control complexity of the axial bearings are considerably reduced by designing the pump with compensation of the axial forces.

Figure 8:
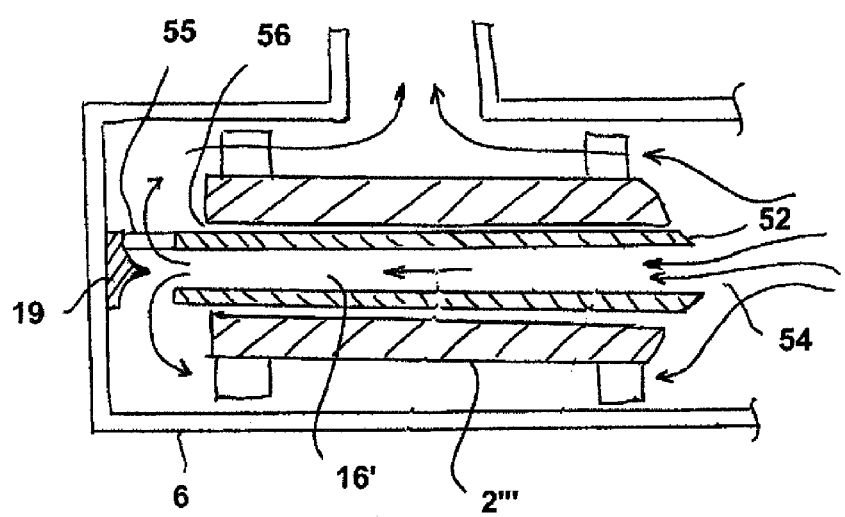
FIG. 8 shows a further longitudinal section of a rotary pump comprising a hollow rotor, which is mounted on a central stator, which is also hollow.

FIG. 8 is a schematic view of a longitudinal section of a pump housing 6 comprising a rotor 2′, the cylindrical cavity of which is pushed on a stationary hollow cylinder 52 and mounted rotatably thereon. The bearing gap 56 can be designed as a hydrodynamic bearing, however it is also possible to provide different bearing mechanisms there, for example sliding bearings. The hollow cylinder 52 is attached at the end-face end of the pump housing 6 in the region of the baffle 19.

Fluid is taken in through the fluid channel 16′ located in the interior of the hollow cylinder 52 from the first end-face end 54 and exits at the second end-face end toward the baffle 19, where it is deflected. The supports 55 of the hollow cylinder allow enough space for the fluid to flow. The rotor 2″ can, in general, be mounted, driven and axially positioned using the same means as already described based on the remaining exemplary embodiments.

The design according to the invention allows all the fluid that is to be transported to be taken in by a fluid chamber, which is located in front of the end-face end of the rotor. From there, the fluid is divided into several partial flows. The overall necessary diameter of the pump housing is thus minimized.

The invention claimed is:

1. A rotary pump comprising a rotor, the rotor having a plurality of delivery elements configured to deliver a fluid parallel to a longitudinal axis of the rotor,
   at least one first delivery element of the delivery elements configured to deliver at least a first portion of the fluid substantially in a first axial direction at an exit of the at least one first delivery element, and at least one second delivery element of the delivery elements configured to deliver at least a second portion of the fluid substantially in a second axial direction at an exit of the at least one second delivery element, the second axial direction opposite the first axial direction, the first axial direction and the second axial direction parallel to the longitudinal axis of the rotor,
   the rotor having a hub that is hollow, the hub comprising a continuous fluid channel formed along the longitudinal axis inside the hub, the continuous fluid channel having an intake opening in a first axial region and a discharge opening in a second axial region, the delivery elements comprising at least one third delivery element, the hub including the at least one third delivery element on an inside wall of the continuous fluid channel, and
   the rotor suspended with at least one of one or more active axial magnetic bearings or an active axial magnetic force of the rotor.

2. The rotary pump according to claim 1, wherein the first axial region is at a first end-face end and the second axial region is at a second end-face end, the first end-face end being axially opposite the second end-face end.

3. The rotary pump according to claim 1, further comprising stationary guides for fluid flows provided on stationary parts of the rotary pump.

4. The rotary pump according to claim 3, further comprising a baffle disposed in an axial extension of the hub for deflecting a fluid flow from the continuous fluid channel into one or more radial directions, the baffle comprising a central elevation.

5. The rotary pump according to claim 1, wherein the first portion of the fluid delivered by the at least one first delivery element of the delivery elements and the second portion of the fluid delivered by the at least one second delivery element of the delivery elements are separated from each other.

6. The rotary pump according to claim 1 or 2, wherein the first portion of the fluid and the second portion of the fluid are separated from each other before contact with the at least one first delivery element of the delivery elements and the at least one second delivery element of the delivery elements.

7. The rotary pump according to claim 1 or 2, comprising a pump housing surrounding the rotor, wherein a plurality of separate fluid channels are provided inside the pump housing, which connect a fluid chamber to various axial sections.

8. The rotary pump according to claim 7, wherein the separate fluid channels connect the fluid chamber to ends of the rotor.

9. The rotary pump according to claim 1 or 2, wherein the first portion of the fluid and the second portion of the fluid are combined after passing through the at least one first delivery element of the delivery elements and the at least one second delivery element of the delivery elements.

10. The rotary pump according to claim 9, wherein the at least one first delivery element of the delivery elements and the at least one second delivery element of the delivery elements deliver the first portion of the fluid and the second portion of the fluid directed toward each other and the first portion of the fluid and the second portion of the fluid are deflected jointly radially to the outside.

11. The rotary pump according to claim 10, wherein the at least one first delivery element of the delivery elements and the at least one second delivery element of the delivery elements are disposed in different sections of the rotor and a volute casing is provided axially between these sections, which surrounds the rotor.

12. The rotary pump according to claim 10, wherein the rotor has a guide at a point where the first portion of the fluid and the second portion of the fluid impinge on each other.

13. A rotary pump comprising:
   a rotor having a plurality of blades, the blades configured to deliver a fluid parallel to a longitudinal axis of the rotor, the blades comprising at least one first blade and at least one second blade, the at least one first blade configured to deliver at least a first portion of the fluid substantially in a first axial direction at an exit end of the at least one first blade, the at least one second blade configured to deliver at least a second portion of the fluid substantially in a second axial direction at an exit end of the at least one second blade, the second axial direction opposite the first axial direction, the first axial direction and the second axial direction parallel to the longitudinal axis of the rotor, the rotor having a hub that is hollow, the hub having a continuous fluid channel formed inside the hub along the longitudinal axis of the rotor, the continuous fluid channel having an intake opening in a first axial region and a discharge opening in a second axial region, the delivery elements comprising at least one third delivery element, the hub including the at least one third delivery element on an inside wall of the continuous fluid channel, the rotor configured to be suspended with at least one of one or more active axial magnetic bearings or an active axial magnetic force of the rotor.

14. The rotary pump according to claim 13, wherein the at least one first blade is disposed helically about the hub of the rotor.

15. A rotary pump comprising:

a rotor having a plurality of blades, the blades configured to deliver a fluid parallel to a longitudinal axis of the rotor, the blades comprising at least one first blade and at least one second blade, the at least one first blade configured to deliver at least a first portion of the fluid in a first axial direction at an exit end of the at least one first blade, the at least one second blade configured to deliver at least a second portion of the fluid in a second axial direction at an exit end of the at least one second blade, the second axial direction opposite the first axial direction, the first axial direction and the second axial direction parallel to the longitudinal axis of the rotor, the rotor having a hub that is hollow, the hub having a continuous fluid channel formed inside the hub along the longitudinal axis of the rotor, the continuous fluid channel having an intake opening in a first axial region and a discharge opening in a second axial region, the delivery elements comprising at least one third delivery element, the hub including the at least one third delivery element on an inside wall of the continuous fluid channel, the at least one first blade disposed helically about the hub of the rotor, and the rotor configured to be suspended with at least one of an active axial magnetic force of the rotor or one or more active axial magnetic bearings.

* * * * *